United States Patent [19]

Perttu et al.

[11] Patent Number: 5,709,215
[45] Date of Patent: Jan. 20, 1998

[54] R-WAVE DETECTION METHOD FOR IMPLANTABLE CARDIOVERTER DEFIBRILLATORS

[75] Inventors: Joseph S. Perttu, Chanhassen; Dennis A. Brumwell, Bloomington; James E. Brewer, Maplewood; Theodore P. Adams, Edina, all of Minn.

[73] Assignee: Angeion Corporation, Plymouth, Minn.

[21] Appl. No.: 524,391

[22] Filed: Sep. 6, 1995

[51] Int. Cl.$^6$ ................................................ A61B 5/0456
[52] U.S. Cl. ................................................ 128/708; 607/5
[58] Field of Search ..................... 607/4, 5, 13; 128/696, 128/702, 704, 708

[56] References Cited

U.S. PATENT DOCUMENTS

| 5,215,083 | 6/1993 | Drane et al. | |
| 5,269,300 | 12/1993 | Kelly et al. | |
| 5,312,443 | 5/1994 | Adams et al. | |
| 5,370,124 | 12/1994 | Dissing et al. | 607/28 |
| 5,395,393 | 3/1995 | Wickham | 607/28 |

Primary Examiner—William E. Kamm
Assistant Examiner—Kennedy J. Schaetzle
Attorney, Agent, or Firm—Brad Pedersen

[57] ABSTRACT

An ICD detection method for sensing the occurrence of an R-wave improves the ability to distinguish R-waves from noise through the use of variable declining sensitivity thresholds. The method includes the consideration of the amplitude of at least the previous most recent R-wave to determine a declining threshold of sensitivity used to recognize a subsequent electrical signal as an R-wave. In the method, the amplitude of the previous R-wave may be classified, based upon amplitude, and based upon the classification, a desirable time constant for the declining threshold of sensitivity is provided as an exponential or reverse exponential decay. Alternatively, a piece wise use of various decay formulas may be combined and used to avoid false recognition of noise as an R-wave.

15 Claims, 6 Drawing Sheets

R-WAVE DETECTION METHOD FOR IMPLANTABLE CARDIOVERTER DEFIBRILLATORS

FIELD OF THE INVENTION

The present invention relates to implantable cardioverter defibrillators (ICDs) and, in particular, the present invention relates to systems for detecting R-wave occurrences in order to provide information for identification of cardiac arrhythmias by implantable cardioverter defibrillators.

BACKGROUND OF THE INVENTION

Sudden cardiac deaths presently claim an estimated 400,000 lives annually in the United States. Rapid treatment of potentially catastrophic cardiac conditions can prevent an imminent death result in many instances.

One potentially catastrophic cardiac event is fibrillation, in which the heart attempts to beat so rapidly (for example, more than 220 beats per minute (BPM)) that it ceases to function as a blood pump. Unless an appropriate functional heart beat rate is quickly reestablished death occurs within a couple minutes. An appropriately normal heart beat, i.e. "sinus rhythm", may often be reestablished by application of a large electrical shock on the order of roughly 10 joules or more (defibrillation) to the heart.

Another serious condition is tachycardia or tachyrhythmia, a rapid heartbeat of 125 to 220 BPM which is inefficient and may eventually lead to fibrillation. An appropriately normal beat, "sinus rhythm", may often be reestablished, depending on the tachyrhythmia heart rate encountered, by application of a slightly more rapid rate of very low pacing shocks of less than 100μ joules which "capture" the heart rate and are then slowed again to within the normal rate, or by application of lesser electrical shock on the order of roughly 1 joules (cardioversion) to the heart.

The ability to identify individuals likely to suffer a tachyrhythmia or fibrillation condition has lead to the preventative step of implanting a cardioverting defibrillating device which is electrically attached to the individual's heart. Rather than rely upon the patient or actively attending medical personnel to identify a cardiac fibrillation event and trigger the device to defibrillate the malfunctioning heart, automatic triggering of the implanted cardioverter defibrillation (ICD) device is provided.

The automatic triggering of ICDs may be understood as divided into a two part detection mechanism which attempts first to sense each beat of the heart and second to analyze the pattern of the sensed beats over time by comparing the pattern to various diagnostic models with a goal of accurately assessing the patient's current heart condition. Many times the analytical second part uses logic to also consider the persistence of an undesirable beat rate pattern, the onset rapidity of the undesirable pattern, as well as physiological differences such as temperature changes, pH changes, etc., in the patient. Having classified or identified the undesirable condition, the ICD then provides treatment consistent with the condition identified.

The ability of ICDs to correctly and accurately detect and identify cardiac fibrillation and/or tachyrhythmia is quite important. False positive detection errors will apply an unrequired defibrillation or cardioversion countershock to a heart which in turn is both painful and potentially damaging. One possible cause of a false positive detection error is the naturally accelerated heart rate associated with vigorous exercise. False negative detection errors, on the other hand, will fail to timely apply a countershock to a fibrillating heart and may allow a patient to die for failure to trigger or allow more easily treatable conditions to persist or progress to more dangerous conditions. Alternatively, a temporary false negative may unduly delay application of a defibrillation or cardioversion shock treatment. Prompt detection and application of appropriate treatment, on the order of seconds or tens of seconds, is a key to successful treatment and any delays begin to reduce the likelihood of successful cardioversion and/or defibrillation.

No matter how sophisticated the analysis provided in the second part of the control mechanism, it is clear that sensing of the heart beats is critical. All the second part analytical models have the sensed heart rate as a major input to diagnosis. U.S. Pat. No. 5,312,443 may be viewed as an example of prior art directed to the second part of the detection mechanism and considers incorporation of other patient information in addition to heart rate to improve the analytical portion of the detection mechanism. The present invention, as will be explained subsequently, is concerned with the first part of the detection mechanism, that is, the sensing of each heartbeat.

Monitoring and detection of cardiac function typically involves electrical sensing of muscle and nerve cell depolarization which can be correlated with cardiac muscle contractions. Electrodes implanted in the heart at positions, such as those in which pacing electrodes might be placed, sense an electrical voltage which when considered over time are not unlike a typical surface electrocardiogram, yet are more defined and localized. Specifically, the electrocardiogram waveform under normal conditions includes a P wave, followed by a complex three part waveform called the QRS pattern, and then a T wave. Of these various components, the "R-wave" is a dominant amplitude feature and is therefore most typically used to sense a heart beat. In the second analytical part of the detection mechanism, this information is typically considered in the form of time intervals between R-waves, which is also sometimes termed "R-R intervals." The electrocardiogram also is accompanied by a noise background as well as extraneous noncardiac muscle movement. Typically, R-waves have a peak amplitude in the range of about 5–15 mv during normal sinus rhythm. Typically T-waves have a peak amplitude of about half of the R-wave amplitude. Noise and extraneous muscle typically have peak amplitudes in the range of about 0.1–1 mv.

Most existing models for the first analytical part of the detection mechanism try to avoid recognizing a signal during a refractory period following an R-wave. Although the ability to discriminate R-waves might appear rather straightforward, the task is further complicated by the need to amplify the R-wave and by the most unfortunate tendency of R-wave amplitude to diminish to as little as 20% of normal amplitude (i.e. 1.0 3.0 mv) during fibrillation. In other words, minimal R-wave amplitudes and peak noise levels are nearly indistinguishable in amplitude during fibrillation.

An older generation of detection systems sensed the occurrence of R-wave electrical events as those signals exceeding a preset constant voltage, where the constant voltage was at a fixed and preset amplitude between about 3.4 to 10 mv. Such triggering levels start at roughly 67% of the amplitude of a normal R-wave and are generally too high to be typical noise or T-waves. However, during fibrillation, R-wave amplitude drops off into the range of 0.5 to 2 mv. In turn, the older generation detection systems, having a preset and fixed amplitude detection threshold, were incapable of distinguishing or sensing the diminished or degenerating R-wave events during fibrillation. In other words, in the older generation constant detection threshold detection mechanisms, R-wave information on heart rate tended to become either completely unavailable or at least highly unreliable during fibrillation.

The current generation of detection systems attempt to address the problem of sensing diminishing R-wave amplitudes during fibrillation by employing a sensitivity threshold which starts at a preset amplitude, for example 67% of the preceding R-wave amplitude, and subsequently becomes more sensitive with a detection threshold dropping over time until a "floor" threshold is reached; typically such a floor is set at about 0.3 to 0.5 mv. This floor is intended to prevent the threshold from dropping to such a low level that the increased sensitivity begins to incorrectly detect noise as R-waves. This reduction in threshold amplitude/increase in sensitivity may occur in the form of an exponential decay with a time constant on the order of 1 to 1.5 seconds that is reset after each R-wave event. For example, the current generation "SENTINEL"™ brand ICD device developed by Angeion Corporation employs a detection mechanism in which the initial threshold is a preset percentage of the most recent R-wave peak amplitude and the decay is a standard exponential. The threshold in the "SENTINEL"™ device thus is lowered from an initial level which is a percentage of the most recent R-wave until a constant floor threshold is reached. Another current generation device uses an initial threshold reset and decays with a reverse exponential to a "floor" threshold which is set to a constant level which is greater than the noise level.

One significant deficiency in these current generation ICD devices is encountered when the decay is based upon a fixed time constant and the devices reset the initial threshold after each R-wave detection. The problem is encountered as temporary super-sensitivity when a low amplitude R-wave occurs during normal sinus rhythm or tachycardia. Once the present generation detection mechanisms observe a low amplitude R-wave, for example, less than 3 mv, during a lower heart rate (less than 180 bpm (beats per minute)) then the initial sensitivity threshold is reset at a low level (such as roughly 2 mv or less) and then proceeds to decline to the "floor" level (about 0.3 to 0.5 mv) and may detect noise as a false R-wave. This problem is particularly encountered in situations where the "floor" threshold is quite sensitive (for example a floor setting of 0.4 mv and a noise level of 0.5 or 0.6 mv). The incorrect or false detection of noise then resets the initial threshold sensitivity to an inappropriately low threshold/overly sensitive condition based upon the noise event which has been falsely detected as an R-wave. This inappropriately low threshold/overly sensitive condition persists, potentially initiating electrical shock therapy to the heart based upon noise timing rather than R-wave timing, until a true R-wave is detected and the system then corrects itself.

Thus, there is a need for a detection system less prone to temporary over sensitivity. The increased ability to avoid such false positive readings will increase patient safety and allow increase efficacy and efficiency in ICDs.

SUMMARY OF THE INVENTION

An ICD detection method for sensing the occurrence of an R-wave to improve the ability to distinguish R-waves from noise through the use of variable declining sensitivity thresholds is disclosed. The method includes the consideration of the amplitude of at least the previous most recent R-wave to determine a declining threshold of sensitivity used to recognize a subsequent electrical signal as an R-wave. In the method, the amplitude of the previous R-wave may be classified, based upon amplitude, and based upon the classification, a desirable time constant for the declining threshold of sensitivity is provided as an exponential or reverse exponential decay. Alternatively, a piece wise use of various decay formulas may be combined and used to avoid false recognition of noise as an R-wave.

In accordance with the first aspect of the present invention, the decay is preferably an exponential decay and the plurality of time constants includes at least two time constants. More preferably, the plurality of time constants are two time constants, the first being less than 1 second for use in the decay algorithm when the most recent previously recognized R-wave had an amplitude greater than 10 mv and the second being more than 2 seconds for use when the most recent previously recognized R-wave had an amplitude less than 5 mv. Most preferably, the decay is an exponential decay and the plurality of time constants include at least three time constants: (1) a time constant of less than 1 second for use when the most recent previously recognized R-wave had an amplitude greater than 10 mv; (2) a time constant of more than 2 seconds for use when the most recent previously recognized R-wave had an amplitude less than 5 mv; and (3) a time constant between 1 and 2 seconds, most preferably about 1.5 seconds for use subsequent to an intermediate amplitude for the most recent previously recognized R-wave, i.e. intermediate R-waves considered for these purposes as having an amplitude from about 5 mv to about 10 mv.

In accordance with a second aspect of the present invention, an improved method for R-wave detection in an ICD includes the device implemented steps of: (a) receiving an electrical signal from the electrodes implanted in the heart, and (b) limiting the recognition of electrical signal as an R-wave event to those events in which the amplitude of the electrical signal exceeds a decreasing threshold level and a floor level. Specifically, the improvement of this embodiment has a decreasing threshold level having a first decay from an initial threshold level to an intermediate threshold level; and a second decay, distinct from the first decay, from the intermediate threshold level to the floor level. Preferably, the intermediate threshold level is determined by the amplitude of at least one of the most recent previously recognized R-waves. More preferably, the intermediate threshold level is determined by elapsed time from the most recent previously recognized R-wave. In such an embodiment, the elapsed time to determine the intermediate threshold level is preferably, about 300 milliseconds. In such an embodiment, a variety of decay algorithms may be employed, but preferably the first decay is a reverse exponential and the second decay is an exponential.

In accordance with a third aspect of the present invention, an improved ICD has an automatic diagnostic system including an R-wave sensing system and an analytical diagnostic model for triggering therapeutic treatment of a heart patient. The improved R-wave sensing system of this improved ICD includes means for recording the occurrence time and the amplitude of a first R-wave from electrical signals associated with a heart depolarization event provided by at least two electrodes implanted in a heart and means for establishing a decreasing sensitivity threshold level for sensing the occurrence of a subsequent R-wave and limiting recognition of the electrical signal as a subsequent R-wave event to those events in which the amplitude of the electrical signal exceeds the decreasing threshold level and a floor level, wherein the decreasing sensitivity threshold is variable depending on decreasing the amplitude of the first R-wave. Preferably, the sensitivity threshold is selected from a plurality of mathematical algebraic functions relating amplitude of the first R-wave to a threshold curve criterion, so as to reduce the likelihood of premature false recognition events from signal noise.

The R-wave sensing system in accordance with the present invention begins at a reset initial threshold and also resets the threshold decay rate based upon the detected amplitude of the most recent previous R-wave event. In one particularly preferred embodiment, a plurality of decay rates are available and one of the decay rates is selected based upon the amplitude detected in the most recent R-wave. For example, two different decay rates are made available. The decay rate providing a fast decay rate is selected if the amplitude is high; the decay rate providing a slow decay rate is selected if the amplitude is low. Both decay rates approach a preset, constant "floor" of threshold sensitivity.

In another embodiment, instead of employing a decay function for R-wave amplitude, a two (or more than two) piece wise algorithm for a part of the cardiac cycle is employed. For example, a reverse exponential decay of sensing may be employed for the first 300 ms of the cycle followed by a common exponential decay for the rest of the cycle. The reverse exponential algorithm would keep the sensing threshold relatively high after the T-wave, where upon the algorithm would then be changed to one which keeps the threshold sensing level from dropping too fast toward the floor level. Numerous other algorithms could be substituted for those in the example.

In yet another embodiment, the above embodiments are combined. Specifically, a first decay rate for a first algorithm is selected from a plurality of decay rates based upon the amplitude of the most recently detected R-wave and a second algorithm with a second decay rate is followed after a set time period following the first decay rate, until a preset floor is reached.

DETAILED DESCRIPTION OF THE PREFERRED EMBODIMENTS

Comprehension of the present invention can be gained through reference to the drawings in conjunction with a through review of the following explanation. In order to facilitate a full appreciation of the invention, an overview of the preferred embodiment is initially provided. The overview is followed by more detailed explanation, and, subsequently, operation and use of the invention are described.

The disclosure of U.S. Pat. No. 5,312,443 (issued to Adams et al.) is incorporated herein by reference and addresses identification of cardiac depolarization rates from a sequence of detected R-wave events. The '443 Adams et al patent is also representative of the skill in the art in preparing circuits for ICD devices.

Figure 1:
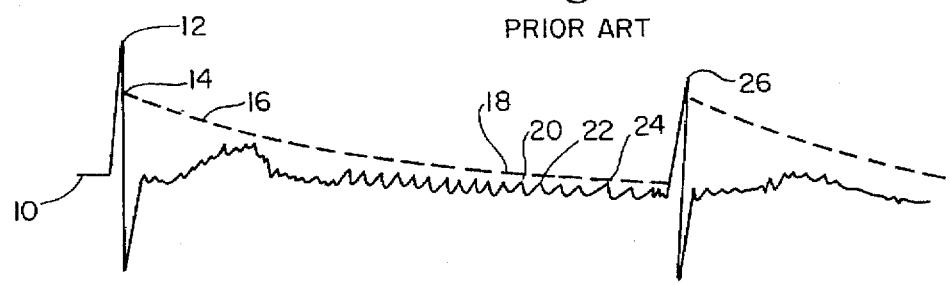
FIG. 1 is a graphical representation of heart rate electrical signals over time from a low heart rate and showing detection threshold sensitivity of a representative present generation ICD.
Figure 2:
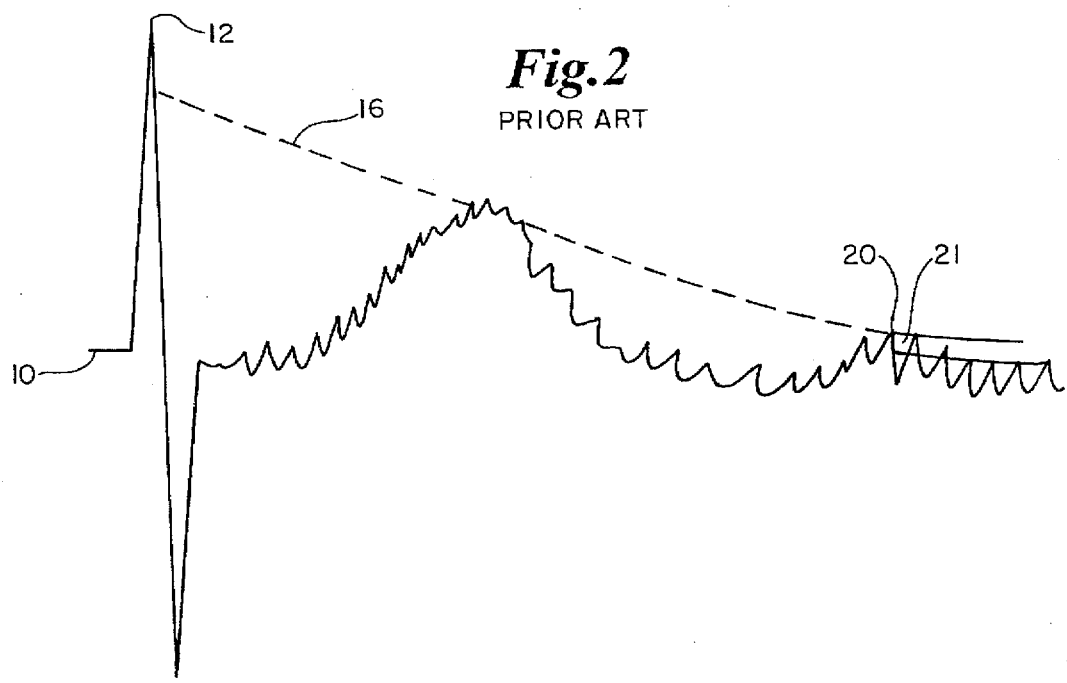
FIG. 2 is an expanded portion of FIG. 1 at 22, and detailing an exemplary over-sensitizing event in a present generation ICD.

The problem to be addressed by the present invention can perhaps be most readily understood by reference to the prior art and shortfalls thereof. In the prior art, an R-wave sensing system of the current generation is depicted in FIGS. 1 and 2. The electrical voltage signal 10 from sensing electrodes implanted in the heart is displayed on the ordinate and plotted over the course of time, along the abscissa. The signal 10 from the implanted electrodes indicates a low amplitude R-wave occurring at 12 with an amplitude of about 3 mv. After the low amplitude R-wave is sensed, the current generation sensing system proceeds to set an initial threshold of sensing 14 at about 2 mv (i.e. about 67% or ⅔ of the most recently detected R-wave 12.) The sensing threshold sensitivity then decays, for example, by an exponential decay algorithm with a decay rate constant of about 1.5 sec as depicted by dotted line 16 until reaching a constant floor 18. Noise in the signal 10 ranges occasionally up to about 0.5 mv. When this exceeds the sensing threshold (dotted line 16) or the floor (dotted line 18) a false detection event is sensed, as shown at 20, 22, and 24, prematurely to the next true R-wave 26. Thus, false data, incorrectly suggesting a highly rapid sequence of R-waves is provided to the analytical portion of the triggering mechanism for consideration in a diagnostic model, potentially resulting in inappropriate therapeutic treatment of the patient's heart. With reference to FIG. 2, this problem is compounded by the resetting of a fresh, and very low, initial sensitivity threshold 21 to about 67% or ⅔ of the amplitude of the false detection event 20. This in turn sets up the next false detection event 22 to follow the refractory period, in large part because of the very low initial sensitivity threshold and also due to the use of the same decay rate constant, 1.5 seconds, from that very low initial sensitivity threshold 21. As soon as the refractory period is completed, the next false detection event 22 can occur.

Figure 3A:
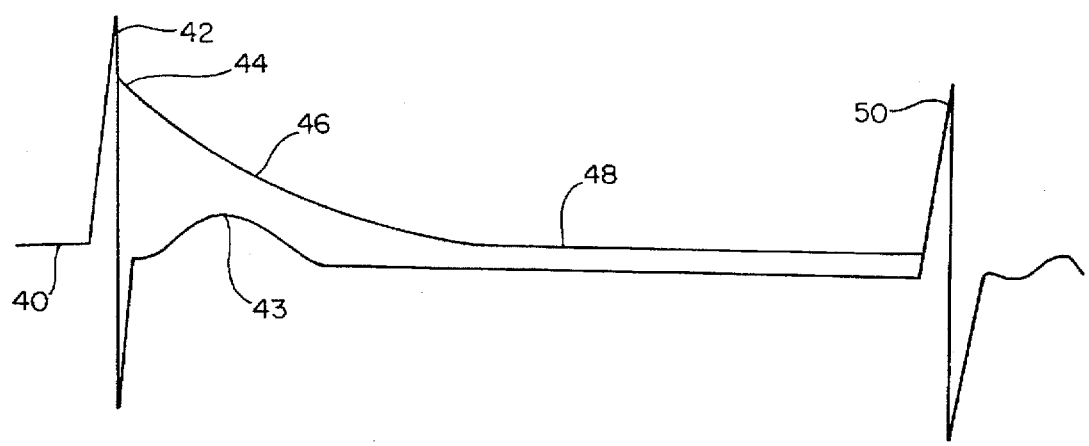
FIG. 3A and 3B depict a variable decay constant detection mechanism of the present invention and the sensitivity threshold of the present invention resulting form a large R-wave event (FIG. 3A) and a small R-wave event (FIG. 3B)
Figure 3B:
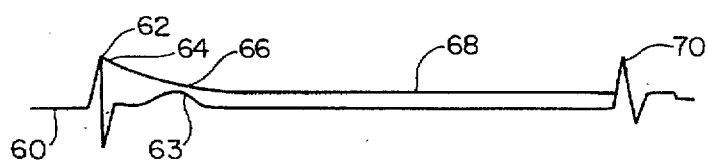
Figure 4:
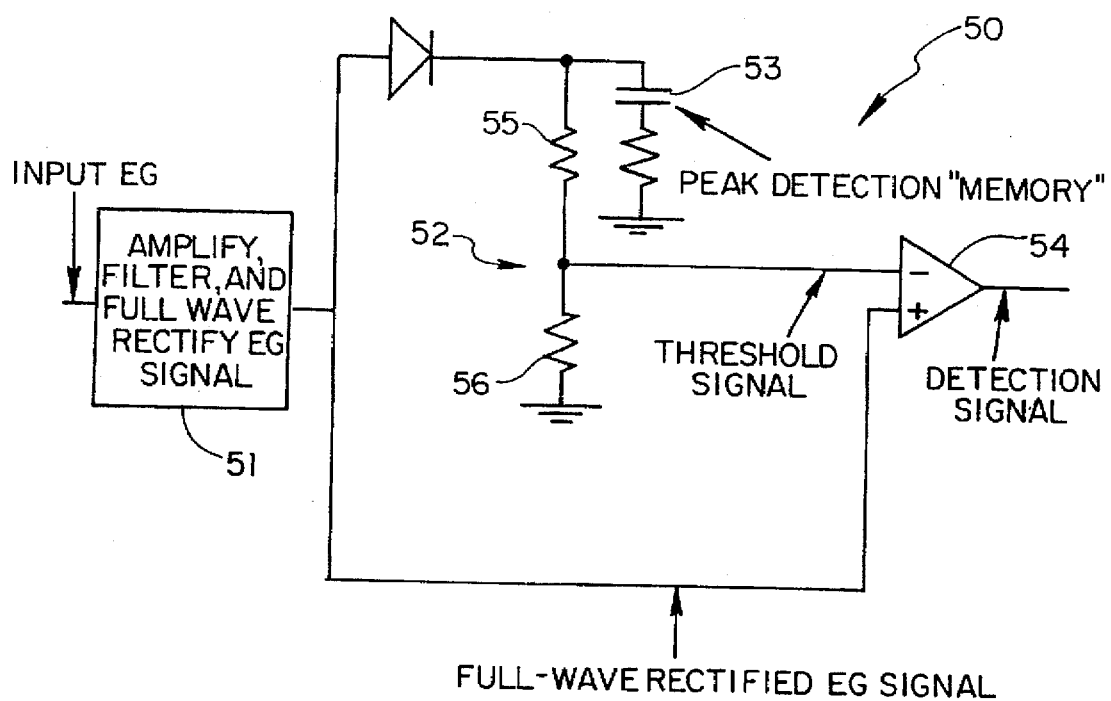
FIG. 4 shows a schematic diagram of a peak detection circuit.

In a first embodiment of the present invention, as shown in FIGS. 3A and 3B, the shortcomings of the prior art sensing systems are overcome as follows: an electrical voltage signal 40, from sensing electrodes implanted in a patient's heart, is displayed on the ordinate and plotted over the course of time along the abscissa. The signal 40 from the implanted electrodes indicates a normal amplitude R-wave occurring at 42 with an amplitude of about 10 mv and a T-wave at 43. After the normal amplitude R-wave is sensed, the current generation sensing system proceeds to set an initial threshold of sensing 44 at about 6.7 mv (i.e. about 67% or ⅔ of the most recently detected R-wave 42.) This is done by a peak detection circuit 50, as is illustrated in FIG. 4. Peak detector circuit 50 comprises an amplifier/filter portion 51, a voltage divider 52, a capacitor 53, and a comparator 54. Voltage divider 52 comprises resistors 55 and 56. Peak detector circuit 50 creates a stored, but slowly decaying signal which represents the peak amplitude of a sensed R-wave. The information is stored as a voltage on capacitor 53, from which the threshold level is derived. The voltage level on capacitor 53 decreases over time at a rate equal to the time constant of the capacitor. The time constant of capacitor 53 is a function of the capacitor and voltage divider 52. While peak detector circuit 50 is shown as implemented with discrete components using a capacitor 53 and comparator 54, it will be appreciated by those skilled in the art that the function of peak detector circuit 50 may be accomplished in a number of ways, including the use of a microconductor and A/P circuits.

Although the initial threshold is preferably set at a ⅔ value, it is possible to utilize any value of between 50 to 95% on most recently detected R-wave 42. The sensing threshold sensitivity then decays, for example, by an exponential decay algorithm with a decay rate constant of a little less than 1.0 second as depicted by complete line 46 until reaching a constant floor (complete line 48.) Noise in the signal 40 again might range occasionally up to about 0.5 mv. In this situation, the noise is unlikely to exceed the sensing threshold (complete line 46) or the floor (complete line 48) so a false detection event is not sensed premature to the next true R-wave 50. Thus, false data, incorrectly suggesting a highly rapid sequence of R-waves is not provided to the analytical portion of the triggering mechanism for consideration in a diagnostic model and the potential for inappropriate therapeutic treatment of the patient's heart is not present.

It will be understood that the first embodiment, after sensing a normal amplitude R-wave provides a sensitivity threshold above the level which might be affected by noise so as to result in a false and premature R-wave sensing. In this respect, it resembles the current generation ICDs. Continuing on with the description of the first embodiment, the difference from the prior art will become apparent. As shown in FIG. 3B, the shortcomings of the prior art sensing systems may be largely overcome as follows: In FIG. 3B, an electrical voltage signal 60 from sensing electrodes implanted in a patient's heart is displayed on the ordinate and plotted over the course of time, along the abscissa. The signal 60 from the implanted electrodes indicates a low amplitude R-wave occurring at 62 with an amplitude of about 1 mv and a T-wave at 63. After the low amplitude R-wave is sensed, like the current generation sensing systems, the first embodiment proceeds to set an initial threshold of sensing 64 at about 0.67 mv (i.e. about 67% or ⅔ of the most recently detected R-wave 62.) Departing, however, from the similarity to the current generation systems, the sensing threshold sensitivity then again decays, but not by the fast time constant applied to normal amplitude R-wave as described with respect to FIG. 3A. Instead, the sensitivity threshold decays at a different and slower rate, for example, by an exponential decay algorithm with a decay rate constant of a little more than 2.0 second as depicted by intermittent line 66 until reaching a constant floor (intermittent line 68.) Noise in the electrical signal 60 again might range occasionally up to about 0.5 mv. In this situation, the noise is unlikely to exceed the sensing threshold (intermittent line 66) or the floor (intermittent line 68) so a false detection event is still not sensed, premature to the next true R-wave 70, even though it is another low amplitude R-wave.

Thus, in this first embodiment when a low R-wave is encountered, false data, incorrectly suggesting a highly rapid sequence of R-waves is not provided to the analytical portion of the triggering mechanism for consideration in a diagnostic model and the potential for inappropriate therapeutic treatment of the patient's heart remains greatly reduced. Moreover, if the diagnostic model does classify the patient's heart situation as requiring therapy, then accurate R-wave event timing information is available for precise timing of the application of therapeutic electrical stimulation. Note also that T-waves 43 and 63 are avoided in both FIGS. 3A and 3B.

Figure 5:
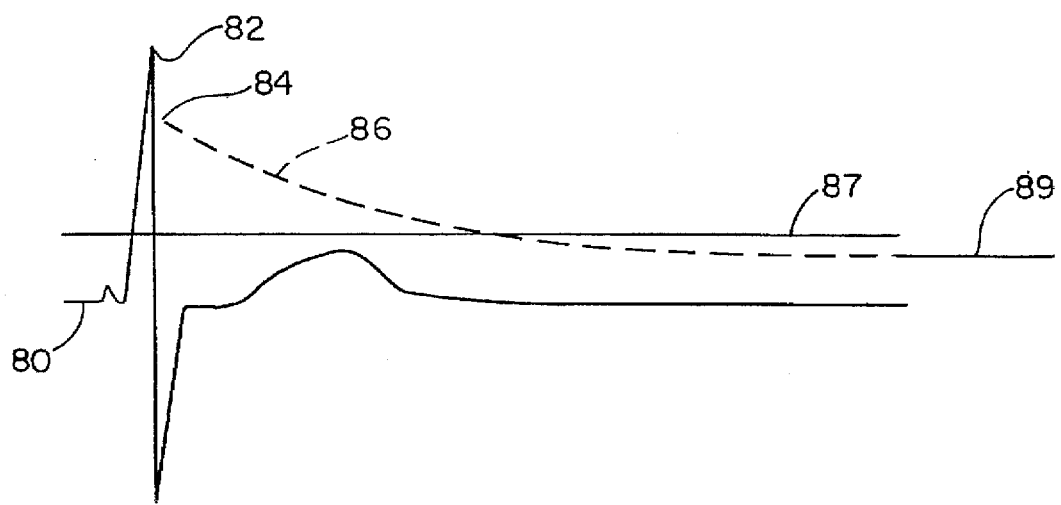
FIG. 5 shows another detection mechanism of the present invention with an initial fast decay rate and a subsequent slow decay rate, with the change in decay rates occurring at a particular intermediate threshold.

In a second embodiment, schematically depicted in FIG. 5, the shortcomings of the prior art sensing systems may also be largely overcome as follows: an electrical voltage signal 80 from sensing electrodes implanted in a patient's heart is displayed on the ordinate and plotted over the course of time, along the abscissa. The signal 80 from the implanted electrodes indicates a low amplitude R-wave occurring at 82 with an amplitude of about 1 mv and a T-wave 83. After the low amplitude R-wave is sensed, like the current generation sensing systems, the second embodiment proceeds to set an initial threshold of sensing 84 at about 0.67 mv (i.e. about 67% or ⅔ of the most recently detected R-wave 82.) Departing, however, from the similarity to the current generation systems, the sensing threshold sensitivity then again decays, first by a relatively fast decay, such as is used with a normal amplitude R-wave. A most preferred first decay is a reverse exponential. However, unlike the single decay current generation systems, once the first decay 86 drops to a predetermined sensitivity level 87, a second decay 88 begins. The second decay 88 is at a slower rate. In a most preferred embodiment, the second decay is by a common exponential decay. A floor 89 is preferably also present. Note also that T-wave 83 is avoided in this embodiment.

Figure 6:
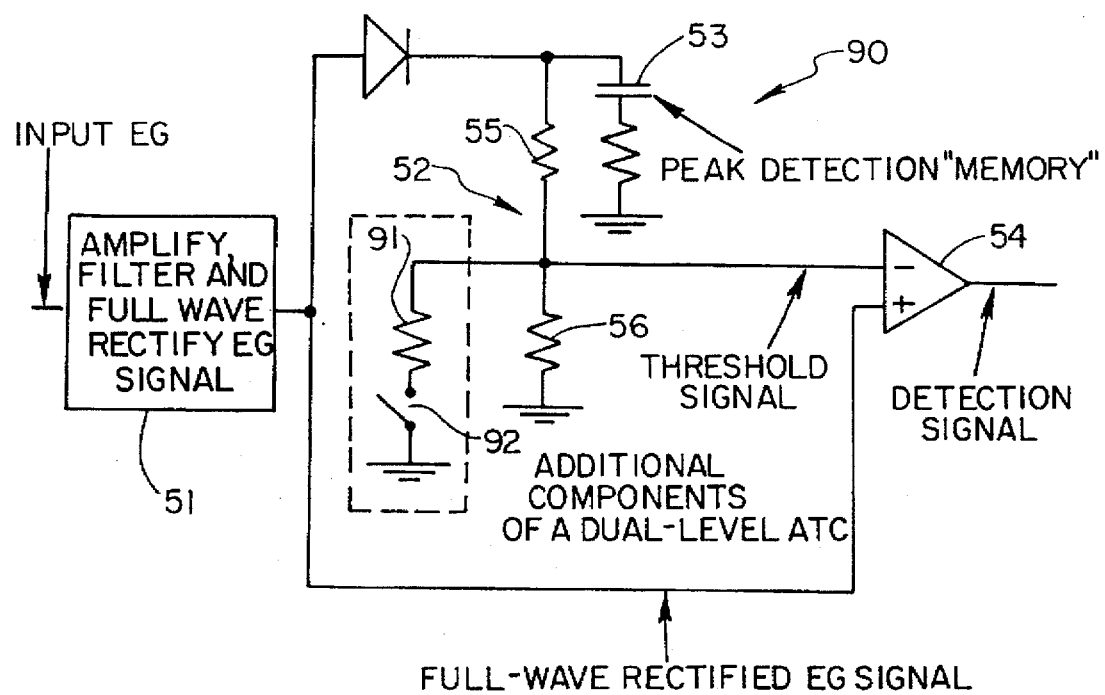
FIG. 6 shows a schematic diagram of a modified peak detection circuit.

To provide for multiple decay rates, a slightly modified peak detector circuit 90 is provided, as is illustrated in FIG. 6. Since peak detector circuit 90 is very similar to peak detection circuit 50 from FIG. 4, like elements will have the same reference numerals. Peak detection circuit 90 has all of the elements of circuit 50 and adds a resistor 91 and a switch 92. As stated above, the time constant of capacitor 53 is a function of the capacitor and voltage divider 52. At a specified time, resistor 91 is switched into the circuit by switch 92 and voltage divider 52 is then changed. This changes the time constant which causes a change in the decay rate.

Figure 7:
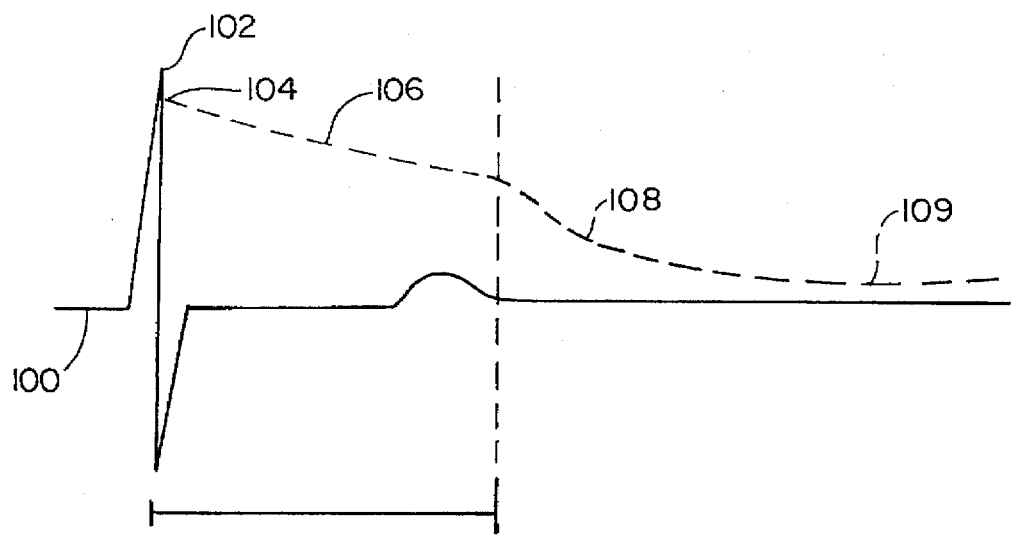
FIG. 7 shows another detection mechanism in which a change in time constants of decay rates occurs after a an elapsed time period from the most recent R-wave detection.

In a third embodiment, schematically depicted in FIG. 7, the shortcomings of the prior art sensing systems may also be largely overcome as follows: an electrical voltage signal 100 from sensing electrodes implanted in a patient's heart is displayed on the ordinate and plotted over the course of time, along the abscissa. The signal 100 from the implanted electrodes indicates a low amplitude R-wave occurring at 102 with an amplitude of about 1 mv and a T-wave 103. After the low amplitude R-wave is sensed, like the current generation sensing systems, the second embodiment proceeds to set an initial threshold of sensing 104 at about 0.67 mv (i.e. about 67% or ⅔ of the most recently detected R-wave 102.) Departing, however, from the similarity to the current generation systems, the sensing threshold sensitivity then again decays, first by a relatively slow decay, such as is used with a normal amplitude R-wave. However, unlike the single decay current generation systems, once the first decay 106 is allowed to drop for a predetermined time period, such as for example 300 milliseconds, and preferably in a range of 275 to 325 milliseconds, a second decay 108 is begun. The second decay 108 drops until, preferably, it reaches a floor 109. In this situation, the noise is unlikely to exceed the sensing threshold. Note also that T-wave 103 is avoided in this embodiment.

Figure 8:
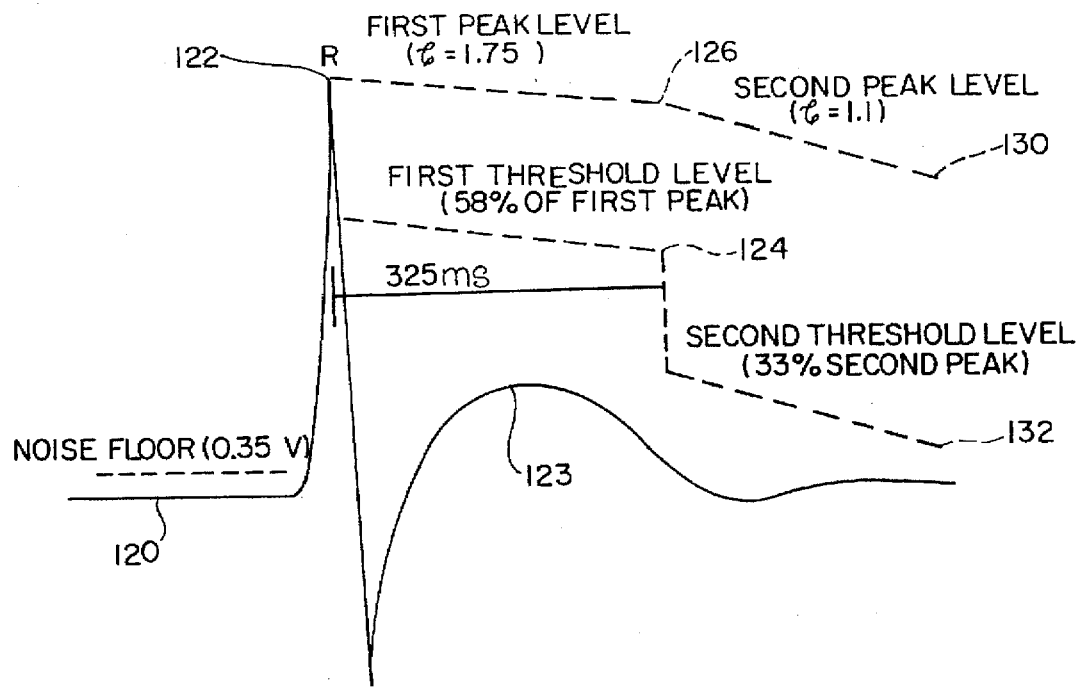
FIG. 8 shows another detection mechanism in which a change in time constants of decay rates occurs after an elapsed time period from the most recent R-wave detection.

A fourth alternative embodiment is schematically depicted in FIG. 8. The fourth alternate embodiment is similar to the third alternate embodiment yet is applicable to R-waves having amplitudes ranging from ±1 mv to ±20 mv. An electrical voltage signal 120 from sensing electrodes implanted in a patient's heart is displayed on the ordinate and plotted over the course of time, along the abscissa. As stated above, the amplitude of the R-wave occurring at 122 may range from ±1 mv–±20 mv. Also shown as part of signal 120 is a T-wave 123. For all amplitudes of R-waves, the same two threshold levels and the same two decay constants are used. Specifically, in the preferred alternative embodiment, a first threshold sensing level of 58% of the first peak level, shown at 124, using a first time constant of 1.75 S, shown at 126, for a period of 325 ms after peak detector, time constant of 1.15, shown at 130, and a second threshold sensing level of 33%, shown at 132 is used thereafter.

Preparation of electrical components and provision of software and hardware control of miniaturized computer systems for implementing the above-described embodiments of this invention are well within the present level of skill of this art.

Because numerous modifications may be made of this invention without departing from the spirit thereof, the scope of the invention is not to be limited to the single embodiment illustrated and described. Rather, the scope of the invention is to be determined by appended claims and their equivalents.

What is claimed:

1. An improved detection method for sensing the occurrence of an R-wave associated with a heart beat event from electrical signals provided by at least two electrodes implanted in the heart, the method including the device implemented steps of: (a) receiving an electrical signal from the electrodes implanted in the heart, and (b) limiting recognition of the electrical signal as a R-wave event to those events in which the amplitude of the electrical signal exceeds a decreasing threshold level and a floor level, the improvement to step (b) comprising:

using a time constant of decay, selected from a plurality of time constants, as the decreasing threshold level, each time constant corresponding to a classification of the amplitude of the electrical sign of at least one most recent previously recognized R-wave events.

2. The improvement of claim 1 and wherein the time constant of decay is an exponential decay and the plurality of time constants includes at least two time constants.

3. The improvement of claim 2 and wherein the at least two time constants consist of:

a time constant of less than 1 second, corresponding to a most recent previously recognized R-wave event having an amplitude greater than 10 mv; and a time constant of more than 2 seconds, corresponding to a most recent previously recognized R-wave event having an amplitude less than 5 mv.

4. The improvement of claim 1 and wherein the time constant of decay is an exponential decay and the plurality of time constants includes at least three time constants, consisting of:

a time constant of less than 1 second, corresponding to a most recent previously recognized R-wave having an amplitude greater than 10 mv;

a time constant of more than 2 seconds, corresponding to a most recent previously recognized R-wave having an amplitude less than 5 mv; and a time constant between 1 and 2 seconds, corresponding to a most recent previously recognized R-wave having an amplitude from about 5 mv to about 10 mv.

5. An improved detection method for sensing the occurrence of an R-wave associated with a heart beat event from electrical signals provided by at least two electrodes implanted in the heart, the method including the device implemented steps of: (a) receiving an electrical signal from the electrodes implanted in the heart, and (b) limiting recognition of the electrical signal as an R-wave event to those events in which the amplitude of the electrical signal exceeds a decreasing threshold level and a floor level, the improvement to step (b) comprising:

using a first decay as the decreasing threshold level from an initial threshold level to an intermediate threshold level; and using a second decay, distinct from the first decay, as the decreasing threshold level from the intermediate threshold level to the floor level.

6. The improvement of claim 5 and wherein the intermediate threshold level is determined by an amplitude of at least one of the most recent previously recognized R-waves.

7. The improvement of claim 5 and wherein the intermediate threshold level is determined by an elapsed time from the most recent previously recognized R-wave.

8. The improvement of claim 7 and wherein the elapsed time to determine the intermediate threshold level is about 300 milliseconds.

9. The improvement of claim 5 and wherein the first decay is a reverse exponential and the second decay is an exponential.

10. The improvement of claim 5 and wherein the second decay is greater than the first decay.

11. The improvement of claim 5 wherein the initial threshold level is approximately 58% of an amplitude of the most recent previously recognized R-wave.

12. The improvement of claim 11 wherein the amplitude of the most recent previously recognized R-wave has second peak level at the intermediate threshold level and wherein the second decay for decreasing the threshold level begins at approximately 33% of the second peak level.

13. An improved detection method for sensing the occurrence of an R-wave associated with a heart beat event from electrical signals provided by at least two electrodes implanted proximate the heart, the method including the device-implemented steps of: (a) receiving an electrical signal from the electrodes, and (b) limiting recognition of the electrical signal as an R-wave event to those event in which the amplitude of the electrical signal exceeds a decreasing threshold level and a floor level, the improvement to step (b) comprising:

(b1) using a first threshold having a first sensitivity for a first portion of the decreasing threshold level; and (b2) using a second threshold having a second sensitivity for a second portion of the decreasing threshold level.

14. The method of claim 13 wherein the first sensitivity is reduced as compared to the second sensitivity.

15. The method of claim 13 wherein the first portion corresponds to a portion of the electrical signal associated with a T-wave event.

* * * * *